United States Patent [19]

Slocum

[11] 4,383,335
[45] May 17, 1983

[54] ROBE ADAPTED FOR INCONTINENT INDIVIDUALS

[76] Inventor: Patricia K. Slocum, 1919 Annette La., Los Altos, Calif. 94022

[21] Appl. No.: 871,831

[22] Filed: Jan. 24, 1978

[51] Int. Cl.³ .................................................. A41B 9/00
[52] U.S. Cl. ............................................ 2/114; 2/69; 2/74; 2/DIG. 7
[58] Field of Search .................... 2/114, 74, 105, 69.5, 2/DIG. 7, 69, 69.5

[56] References Cited

U.S. PATENT DOCUMENTS

| | | | |
|---|---|---|---|
| 2,886,822 | 5/1959 | Matthews | 2/114 |
| 3,144,659 | 8/1964 | Matthews | 2/114 |
| 3,557,385 | 1/1971 | Hendrickson | 2/114 |

*Primary Examiner*—Doris L. Troutman
*Attorney, Agent, or Firm*—Richard Alan Brown

[57] ABSTRACT

A robe adapted for use by incontinent individuals having a front panel extending continuously from the neck downward to about the feet of the wearer and extending across the front of the body of the wearer; upper rear panel forming sections from either edge of the front panel around the sides and across the back of the wearer to the middle of the back, and including means for securing together the upper sections; sleeves having first ends secured between the front panel and the upper rear panel-forming sections with longitudinal openings extending throughout the length thereof and being shaped to cover at least the shoulders of the wearer; lower rear panel forming sections extending from either edge of the lower part of the front panel, the lower sections being adapted for wrapping around the legs of the wearer; and, the upper and the lower sections being spaced apart along the edges of the front panel such that the upper and lower rear panel forming sections separate when worn in a sitting position so as not to expose any part of the robe beneath the buttocks of the wearer when seated.

3 Claims, 4 Drawing Figures

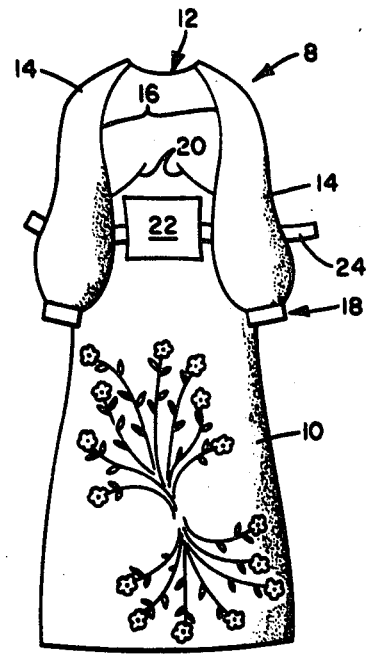
FIG_1
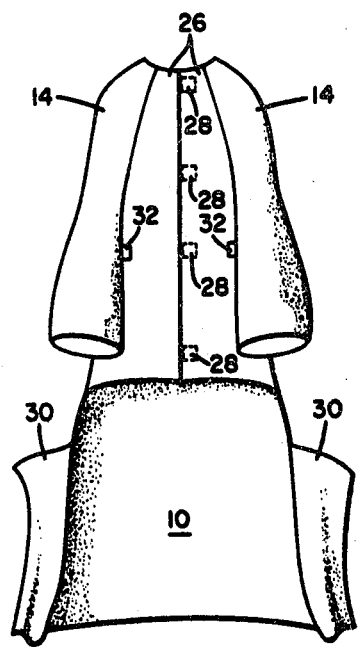
FIG_2
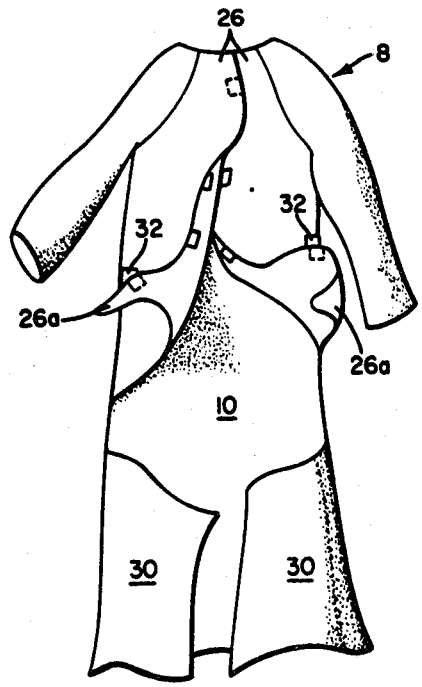
FIG_3
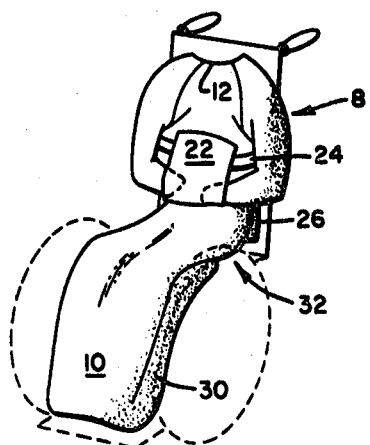
FIG_4

ROBE ADAPTED FOR INCONTINENT INDIVIDUALS

BACKGROUND OF THE INVENTION

1 Field of the Invention

This invention generally relates to gowns adapted for patients, and particularly adapted to incontinent individuals confined to a wheelchair or the like.

2. Description of the Prior Art

As noted in prior patents dealing with related subject matter, dress is an existing problem in private homes and in institutions that take care of numerous disabled persons. Whether the disability is caused by accident, illness or disease (mental or physical) or some other defect, many patients are unable to dress themselves in usual clothing. Some are bed-ridden or confined to wheelchairs. Still other patients are restricted in the clothing they can wear due to their illness or disease, such as for example, incontinent patients. Nevertheless, many of these patients wish to be clothed in a garment more attractive in appearance than the conventional hospital gown.

Patients in wheelchairs do not wear plastic pants with disposable or washable liners (as do persons who could walk about) when they have problems of continence of bladder and bowel functions. Such patients sit in a wheelchair on a disposable diaper-like pad which is not fastened to the body. No pants are worn over the pad. The patient is then dressed in whatever gown or robe is readily available. The staff usually scoot these garments up in the rear, so that there is less likelihood of their being soaked, and so that pad changes can be made more easily.

This present practice is inadequate in many ways. There is too much excess material in the rear of the chair seat and too little in front for comfort and decency. Dressed this way the patients look sloppy and are not comfortable, and the incontinence problem is very obvious to the observer. Patients certainly cannot be cared for easily, and the time spent in changing pads and dressing patients is greater than necessary. This incontinent situation is humiliating and depressing for any patient, and the present system simply makes it more so.

Exemplary prior art gowns are described in U.S. Pat. No. 2,712,133 entitled "Wheelchair Robe" by L. M. Coleman; U.S. Pat. No. 974,981 entitled "Combination Garment" by L. S. Lee; U.S. Pat. No. 3,911,499 entitled "Disposable Medical Gown" by J. Benevento and K. W. Hinsch; U.S. Pat. No. 3,855,635 entitled "Two Piece Hospital Gown" by C. Ramirez; and U.S. Pat. No. 3,727,238, entitled "Garment For Invalid" by B. R. Wolfson.

Further, U.S. Pat. No. 2,707,282 by L. M. Paterson teaches a "Hospital Garment" which is utilitarian in appearance. In particular, the garment is of the conventional hospital gown design and has rear overlapping portions adapted to be folded away from beneath a patient when seated.

In U.S. Pat. No. 2,886,822 by C. A. Matthews for a "Hospital Gown" teaches a gown designed for use by a patient when lying in bed. This gown is likewise utilitarian in appearance and was designed primarily to facilitate the dressing of patients, that due to their condition, are either difficult to move or dangerous to move, or for patients restricted to bed.

U.S. Pat. No. 3,144,659 also by C. A. Matthews for a "Hospital Gown" again teaches a utilitarian hospital gown of convential design. As pointed out in this patent, the purpose of such a design is substantially the same as that in his prior patent discussed above.

U.S. Pat. No. 3,339,209 by H. E. Larson for a "One-Piece Garment" teaches a garment eminently suited for disabled women. This one-piece garment is designed to include under support to the chest portion of the wearer and is substantially a dress in design for ambulatory patients. In addition, this garment also teaches the separation of the garment in the back portion thereof for use by incontinent patients; however, this gown still does not provide a readily open area in the rear portion thereof without bundling of material around the patient while seated. As in most conventional hospital gowns or other conventional gowns per se, an incontinent patient will require a portion of the gown to be removed from the seat area when the patient is seated, which removal will cause a bundling appearance of the garment around the patient when seated. As will be described in greater detail herein below, my design is directed to overcome this and other associated problems with the prior art.

SUMMARY OF THE INVENTION

My invention restores the semblence of dignity to the patient, and provides a garment which appears to be an ordinary robe as the patient sits in a wheelchair. To this end, my invention eliminates bulk in the back of the patient while seated, since the back panels of my robe are only long enough to cover the back of the body to the seat of the wheelchair, and with sufficient additional material on the back panels to allow for easy insertion of a bedpan or the like without eliminating warmth, comfort and a modicum of privacy.

Broadly stated, the present invention relates to a robe for individuals having problems of continence of bladder and bowel functions, comprising a front panel extending continuously from the neck downward to about the feet of the wearer and extending across the front of the body of the wearer; upper rear panel forming sections extending from either edge of the front panel around the sides and across the back of the wearer to the middle of the back, and including means for securing together the upper sections; sleeves having first ends secured between the front panel and the upper sections with longitudinal openings extending throughout the length thereof and being shaped to cover at least the shoulders of the wearer; lower rear panel forming sections extending from either edge of the lower part of the front panel, the lower sections being adapted for wrapping around the legs of the wearer; and, the upper and the lower sections being spaced apart along the edges of the front panel such that the upper and lower rear panel forming sections separate when worn in a sitting position so as not to expose any part of the robe beneath the buttocks of the wearer when seated.

It is accordingly an object of the present invention to provide a new and improved gown for incontinent individuals.

It is yet another object of the present invention to provide a gown for incontinent patients which is attractive in appearance while still being utilitarian in function.

It is still another object of the present invention to provide a gown for incontinent patients which is warm and comfortable to the wearer.

It is still a further object of the present invention to provide a gown for incontinent patients which is adapted for receiving means for securing the patient to a wheelchair or the like.

A still further object of the present invention is to provide a robe for incontinent patients attractive in appearance and also including a storage place or pocket to store such things as teeth, hearing aides, glasses and the like.

One feature of the present invention is the provision of separate lower back forming panels independent of upper back forming panels such that the lower back forming panels may be tucked behind legs of the wearer while seated to thereby encircle the legs for warmth and comfort.

Another feature of this invention resides in the provision of separation of the upper back forming panels from the lower back forming panels when the incontinent wearer is seated so as to avoid exposure of any part of the garment to the buttocks while, at the same time, presenting a dignified overall appearance of a complete robe.

An advantage of the present invention is that the patient can be dressed in the robe of this invention without an attendant being hindered by cumbersome fasteners or having to hold the full weight of the body of the incontinent wearer.

Another advantage of this invention is that the back of the garment can be closed with fasteners that do not press upon the body of the wearer in contact with the back of the chair, and remains fastened until unfastened by the attendant, since such fasteners are unaccessible to restless, senile fingers.

These, as well as other object, features and advantages, will become apparent from the following description of my invention taken in conjunction with the drawing.

BRIEF DESCRIPTION OF THE DRAWINGS

In the drawing, forming a part of specification, and wherein like reference numerals are employed to designate like parts throughout the same:

FIG. 1 is a frontal view of the gown of the present invention;

FIG. 2 is a rear view of the gown of the present invention;

FIG. 3 is also a rear view of the gown of this invention showing separation of the upper rear panel forming sections; and, FIG. 4 illustrates the gown being worn by a patient seated in a wheelchair.

DETAILED DESCRIPTION

The present invention will now be described in connection with a garment utilizing quilted or velour materials, which provide for longer wear, are washable and are substantial enough not to require undergarments while still providing warmth. Other suitable materials may also be used. In addition, while the robe described herein below may appear adapted for women, it is noted that my invention is not so limited but may readily be adapted for use by men.

Referring now to FIG. 1, robe 8 of the present invention is shown in a frontal view wherein it may be seen that the robe has a front panel 10 extending from a neck portion 12 down to about the feet of the wearer. The front panel 10 is an A-line style, except for a flare at each edge starting about one inch below the knee, expanding the width of the A-line from that point to about three inches wider at the bottom hem. The sleeves 14 are attached to the front panel 10 by seams 16 extending from the armpit area up to the neck portion area 12, and may be a raglan style as shown. Also, sleeves 14 may have crimped ends 18 at the wrist area of the wearer. Bust darts 20 may be provided on the front panel 10 if the robe is to be used for women. An additional panel 22 is secured to the front panel 10 just below the bust darts 20. In one embodiment, panel 22 forms a pocket and is approximately twelve (12) inches wide by eight (8) inches high and being centered on the garment front 10 about an inch below the points of the bust darts. This pocket meets such needs of the wearer as a place to keep hands warm, or a support for the hands at a height suitable to maintain good circulation or a place to store personal items. The panel 22 has an additional function, as will be described in greater detail hereinbelow, of providing an unobstructive and unobtrusive means for providing a place for insertion of a restraining belt 24 for safely securing the wearer in a wheelchair or the like.

Referring now to FIG. 2, a rear view of the gown 8 is illustrated. Two panel forming sections 26 extend from either edge of the front panel 10 around the sides and across the back of the wearer to the middle of the back. The upper panel sections 26 are secured together by means of fasteners 28. The fasteners 28 are preferrably made of self-attaching strips from a cohesive or adhesive material. In one embodiment it was found satisfactory to use three-quarters (¾) inch medium stress VELCRO fasteners. The upper sections cover the back of the body from the neck to below the line where the back of the body comes in contact with the seat of a wheelchair.

In FIG. 2 the sleeves 14 are shown as having flared ends at the wrist, which is an alternate means for finishing the sleeves. In either form of the sleeves 14, it is preferable to make the sleeves wide enough to permit unfastening of the cuffs for moving the sleeves up the arm for providing access for shots, or the like, or taking blood pressure, etc. Lower rear panel forming sections 30 are shown in FIG. 2 extending from either edge of the lower part of the front panel 10. The lower panel forming sections 30 are independent of the upper panel forming sections 26, and are independent of one another. These lower sections are adapted for wrapping around the legs of the wearer when seated. Each of these panels preferrably have a flare at the side edges thereof to correspond with the flare of the front panel 10 if such flare is made into the garment. These panels in one embodiment are twenty-two (22) inches in length and thirteen (13) inches at the top width (all are finished dimensions).

Referring now to FIG. 3, upper rear panel sections 26 are illustrated as having additional VELCRO fasteners 32 in proximity to the common edge between the panels 26 and the front panel 10. These additional fasteners provide a means for securing corners 26a of the panels 26 away from the buttocks area, while attending to the wearer. In particular, VELCRO fasteners 28 on the upper rear panel sections 26 mate with the VELCRO fasteners 32.

Referring now to FIG. 4, the robe 8 is shown about a wearer, while seated in a wheelchair. Note that the panel 22 is adapted for receiving the restraining belt 24, which secures the wearer in the wheelchair to keep the individual from sliding or falling out of the wheelchair, as well as providing for a support for the hands of the wearer. Note also, that the lower rear panel forming sections 30 will tuck around behind legs of the wearer to keep the wearer warm while seated in the wheelchair. It is also noted that upper rear panel forming sections 26 separate from the lower rear panel forming sections 30 in area 32 while the wearer is seated, so as not to expose any part of the robe 8 beneath the buttocks of the wearer while seated.

It will, of course, be understood that modifications of the present invention, and its various aspects will be apparent to those skilled in the art, some being apparent only after study, and others being matters of routine garment design. Accordingly, the scope of the invention should not be limited by the particular embodiment and specific construction herein described, but should be defined only by the appended claims, and equivalents thereof.

Various features of the invention are set forth in the following claims.

What is claimed is:

1. A robe for incontinent individuals comprising:
   (a) a front panel extending continuously from the neck downward to about the feet of the wearer and extending across the front of the body of the wearer;
   (b) upper rear panel forming sections extending from either edge of said front panel around the sides and across the back of the wearer to the middle of the back, and including means for securing together said upper sections;
   (c) sleeves having first ends secured between said front panel and said upper sections with longitudinal openings extending throughout the length thereof and being shaped to cover at least the shoulders of the wearer;
   (d) lower rear panel forming sections extending from either edge of the lower part of the front panel, said lower sections being adapted for wrapping around the legs of the wearer; and
   (e) said upper and said lower sections being spaced apart along the edges of said front panel such that the upper and lower rear panel forming sections separate when worn in a sitting position so as not to expose any part of the robe beneath the buttocks of the wearer when seated.

2. A robe as in claim 1 further characterized by additional securing means being provided near seams between said front panel and said upper panel forming sections for securing bottom corners of said upper sections when said corners are folded away.

3. A robe as in claim 1 further characterized by said front panel including an additional panel attached thereto and extending across said front panel between the waist and bust lines of the robe, so as to form means for receiving a safety belt securing a wearer in a chair.

* * * * *